US00PP27286P3

(12) United States Plant Patent
Suphachadiwong

(10) Patent No.: US PP27,286 P3
(45) Date of Patent: Oct. 18, 2016

(54) ***VANDA* PLANT NAMED 'SPCDW1320'**

(50) Latin Name: ***Vanda* hybrid**
Varietal Denomination: SPCDW1320

(71) Applicant: Thumrong Suphachadiwong, Chonburi (TH)

(72) Inventor: Thumrong Suphachadiwong, Chonburi (TH)

( * ) Notice: Subject to any disclaimer, the term of this patent is extended or adjusted under 35 U.S.C. 154(b) by 88 days.

(21) Appl. No.: 14/544,031

(22) Filed: Nov. 17, 2014

(65) Prior Publication Data

US 2015/0143596 P1 May 21, 2015

(30) Foreign Application Priority Data

Nov. 19, 2013 (QZ) ..... PBR 2013/2929

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

'SPCDW1320' is a distinctive variety of *Vanda* which is characterized by the light-yellow sepal and petal background coloration, purple spotting and a broad rim of purple on each of the sepals and petals, with the light yellow background being more prominent in the two lateral sepals than in the two petals and the dorsal sepal. The new variety is a *Vanda*, typically produced as an indoor ornamental plant.

3 Drawing Sheets

Latin name of the genus and species: The Latin name of the genus and species of the novel variety disclosed herein is *Vanda* hybrid.

Variety denomination: The inventive variety of *Vanda* disclosed herein has been given the variety denomination 'SPCDW1320'.

BACKGROUND OF THE INVENTION

This application relates to a new cultivar of *Vanda*, as described in EU application number 2013/2929, filed Nov. 19, 2013, grant pending, to which applicant claims priority.

Parentage: The *Vanda* variety 'SPCDW1320' is the result of a planned breeding program. The new variety originated as a seedling from the crossing of the unpatented, proprietary seed parent *Vanda* 'M58N' with the unpatented, proprietary pollen parent referred to as *Vanda* 'S399'. The crossing was made by the inventor in his research greenhouse in Chonburi, Thailand in October of 1999.

The new variety was first selected by the inventor, Thumrong Suphachadiwong, a citizen of Thailand, in February of 2005, in a research greenhouse belonging to the inventor in Chonburi, Thailand. After identifying the new variety as a potentially interesting selection, the inventor continued confidential testing and propagation of 'SPCDW1320', assessing stability of the unique characteristics of this variety.

Asexual Reproduction: Asexual reproduction of the new cultivar 'SPCDW1320' was first performed at a commercial laboratory belonging to the inventor in Chonburi, Thailand by tissue culture in June of 2007. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1320' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1320'. These characteristics in combination distinguish 'SPCDW1320' as a new and distinct *Vanda* cultivar:

1. Unique sepal and petal coloration, namely a light yellow background with purple spotting and a broad rim of purple of each of the sepals and petals; and,
2. A unique light yellow background being more prominent in the two lateral sepals then in the two petals and the dorsal sepal; and,
3. Very dark purple floral lip.

BOTANICAL DESCRIPTION OF THE PLANT

Figure 1:
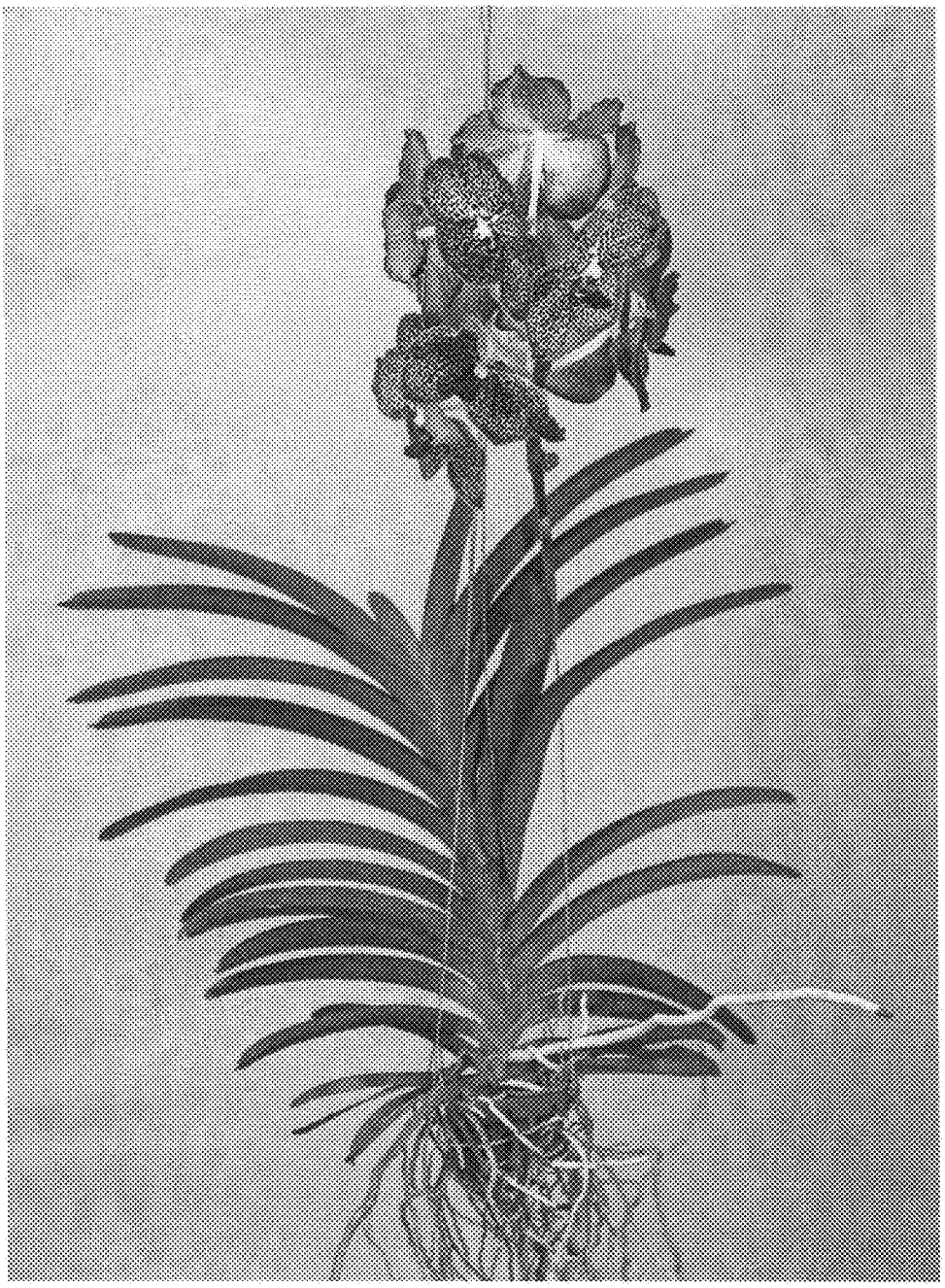
FIG. 1 illustrates, as nearly true as it is reasonably possible to make the same in color photographs of this type, an exemplary plant of 'SPCDW1320' grown in a commercial greenhouse in Honselersdijk, the Netherlands. This plant is approximately 5.5 years old, shown planted in an 8 by 8 cm container.
Figure 2:
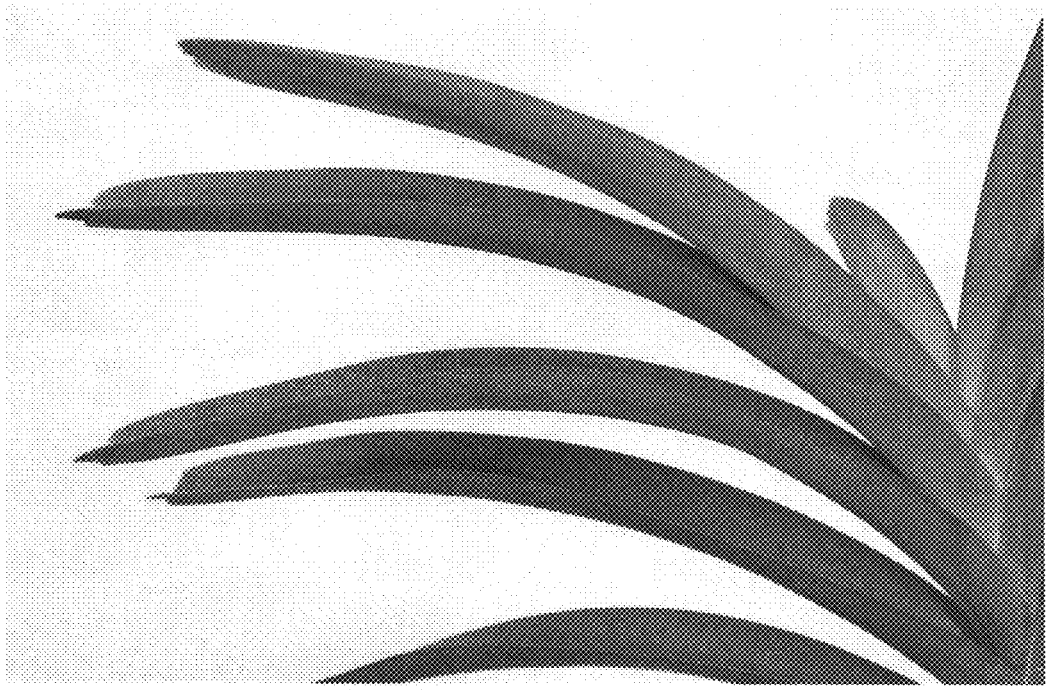
FIG. 2 illustrates, in full color, the typical foliage of 'SPCDW1320'.
Figure 3:
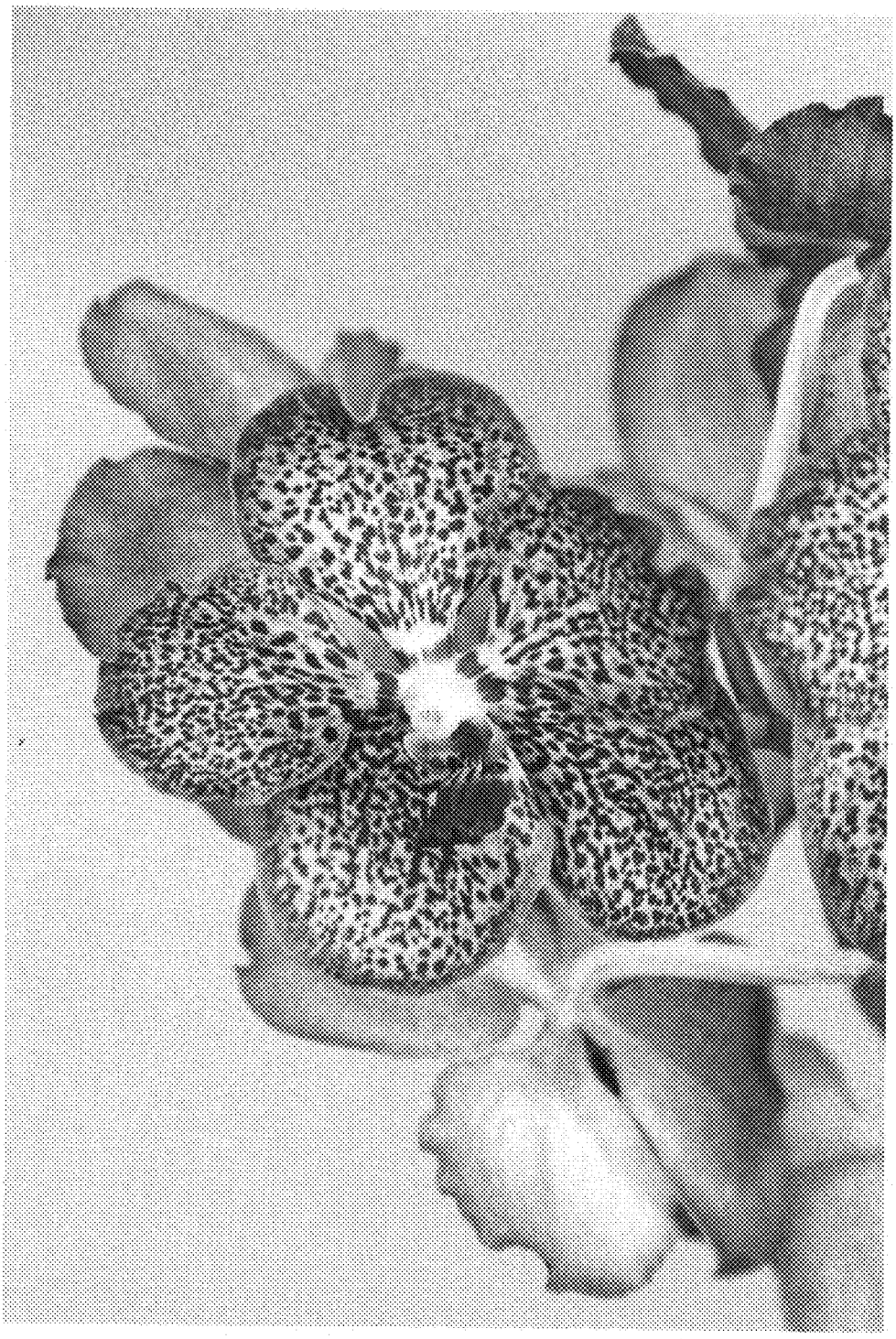
FIG. 3 illustrates, in full color, the typical flowers of 'SPCDW1320'.

The following observations and measurements describe 'SPCDW1320' plants grown in a greenhouse in Honselersdijk, the Netherlands. Temperatures ranged were approximately 23 degrees Celsius during the day and 19 degrees Celsius at night. No photoperiodic or chemical treatments were given to the plants. When natural lighting fell below 150 Watt, artificial lighting is given at 10,000 lux for 16 hours a day. Measurements and numerical values represent averages of typical plant types.

Those skilled in the art will appreciate that certain characteristics will vary with older or, conversely, with younger plants. 'SPCDW1320' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'SPCDW1320' and comparisons with other varieties of *Vanda* are provided below.

Technical description of the variety.

Plant description:

*Growth habit*.—Monopodial, upright.

*Average height from base (plant grown in hanging basket, so no soil line present) to top of foliage*.—42.5 cm.

*Average height from base (plant grown in hanging basket, so no soil line present) to top of flowers*.—53.0 cm.

*Plant spread*.—Average of 59.1 cm.

*Normal pot size*.—Hanging basket (8 by 8 cm square).

*Growth rate*.—Moderate.

*Number of leaves per plant*.—Average of 30.

*Propagation type*.—Tissue Culture.

*Propagation details*.—The time needed from for the start of a mericlone to get the small plants ready for deflasking is approximately 24 months under a controlled temperature of about 26 degrees Celsius. After that period plants have matured roots. Plants start to make roots in the last 6 months in flasks. After deflasking they remain in a shaded and controlled environment.

*Disease resistance*.—Good resistance to the normal diseases found in *Vanda*.

*Drought tolerance and cold tolerance*.—Drought tolerance is typical for species. Superior cold tolerance, to approximately 6 degrees Celsius.

Root system: Moderately to heavy rooting with aerial roots only. Roots very fleshy, non-fibrous. Average length of old roots is 60.7 cm, average diameter of old roots is 0.3 cm, average diameter of young roots is 0.6 cm. Old roots colored yellow-green; near RHS 146B. Young roots colored greyed-green; near RHS 192A to 192B, growing tips of roots yellow-green; 146A.

Foliage:

*Arrangemen*.—Distichous.

*Average length*.—Approximately 25.7 cm.

*Average width*.—Approximately 2.9 cm.

*Shape of blade*.—Ligulate, strongly carinate.

*Aspect*.—Moderately curved.

*Apex*.—Unequal praemorse.

*Base*.—Sheathing.

*Sheath length*.—Average 2.5 cm.

*Sheath width*.—Average 1.3 cm.

*Sheath color*.—Green; near RHS 143C.

*Margin*.—Entire.

*Texture of top surface*.—Glabrous, very slightly glossy.

*Texture of bottom surface*.—Glabrous, matte.

*Color of young foliage, upper side*.—Green to yellow-green; in between near RHS 143A and 146A.

*Color of young foliage, under side*.—Yellow-green to green; in between near RHS 143A and 146A.

*Color of mature foliage, upper side*.—Green; near RHS N137A.

*Color of mature foliage, under side*.—Yellow-green; near RHS 146A and 146B.

*Venation*.—Parallel.

*Venation coloration*.—As leaf surface; upper side green; near RHS N137A, under side yellow-green; near RHS 146A and 146B.

*Petiole*.—No petioles present, leaves sessile.

Inflorescence:

*Flowers per stem*.—Average of 10.

*Inflorescence arrangement*.—Axially placed raceme.

*Inflorescence height*.—Approximately 28.2 cm (measured from base of lowest flower to top of upper flower).

*Inflorescence width*.—Approximately 19.9 cm.

*Peduncle*.—Length — Approximately 46.3 cm. Width — Approximately 0.7 cm. Aspect — Approximately 20° angle to rosette. Strength — Strong. Texture — Smooth, moderately glossy. Color — Green; near RHS 143B.

Bud:

*Rate of opening*.—Buds open approximately three weeks from first sight.

*Length*.—Average of 1.9 cm.

*Diameter*.—Average of 1.7 cm.

*Shape*.—Broad obovate.

*Color*.—Violet-blue; near RHS 91A and 91B tinged yellow-green; 150D, base yellow-green; near RHS 150C to 150D.

Flower:

*Flower type*.—Zygomorphic (orchidaceous), typical shape for the genus *Vanda*.

*Shape*.—Zygomorphic, consisting of three sepals and three petals, one of which is transformed into a labellum (lip).

*Length (height)*.—Approximately 11.4 cm.

*Width*.—Approximately 11.1 cm.

*Depth*.—Approximately 3.6 cm.

*Fragrance*.—No fragrance.

*Lastingness*.—6 to 8 weeks, depending on growing conditions.

*Persistent*.—No.

*Quantity of petals*.—3 (2 "traditional" petals and a labellum (lip), described separately).

*Petals*.—Arrangement — one lateral petal on each side. Length — Approximately 5.1 cm. Width — Approximately 4.7 cm. Shape — Broad ovate. Apex — Obtuse. Base — Cuneate. Margin — Entire, slightly to moderately undulate. Texture of Upper forward surface — Glabrous, matte, velvety. Texture of Lower back surface — Glabrous, matte, velvety. Color When opening, forward surface — Violet; near RHS 85D, lower half (side towards lateral sepal) greyed-yellow; near RHS 160D. Petal marbled purple-violet; near N82B to N82C, and heavily dotted purple; near RHS 79A. Color When opening, back surface — Greyed-yellow; near RHS 160D, with an unclear reticulate veining colored violet-blue; near RHS 90B to 90C. Color When Fully Opened, forward surface — White; near RHS N155A, lower half (side towards lateral sepal) yellow-green; near RHS 145C. Petal marbled violet; near N88C, and heavily dotted purple; near RHS 79A. Color When Fully Opened, back surface — Violet-blue; near RHS 91C to 91D, lower half (side towards lateral sepal) green-white; 157C to 157D, with an unclear reticulate veining colored violet-blue; near RHS 90D. Fading, forward surface — Not fading. Fading, back surface — Not fading. Color Venation Fully Opened, forward surface — Veins not visible, colored as petal surface. Color Venation Fully Opened, back surface — Main vein violet-blue; near RHS 90C, other veins as petal surface.

*Labellum/lip*.—Shape — Three-lobed, lateral lobes involute, central lobe very slightly revolute. Length — Approximately 2.1 cm (excl. spur). Width — Approximately 1.7 cm. Texture — Glabrous, slightly glossy, with 3 callosities. Apex — Emarginate to straight. Base — Cuneate. Color When Opening, forward surface — Lateral lobes yellow-green; near RHS 151D, blushed and dotted purple; near RHS N77A and N77C. Central lobe greyed-purple; near RHS N186B, callosities purple; near RHS 79A with a yellow-green base; near RHS 145D. Color When Opening, back surface — Lateral lobes yellow-green; near RHS 145C flushed purple; near RHS N77C. Central lobe violet-blue; near RHS N92A, base yellow-green; near RHS 145B. Color When Fully Opened, forward surface — Lateral lobes yellow-green; near RHS 151C, blushed and dotted purple; near RHS N77A. Central lobe greyed-purple; near RHS N186B, callosities violet; near RHS 83A, with a yellow-green base; near RHS 145C. Color When Fully Opened, back surface — Lateral lobes yellow-green; near RHS 145B flushed purple; near RHS N77C and N77D. Central lobe violet-blue; near RHS N92A, base yellow-green; near RHS 145C. Fading, forward surface — Not fading. Fading, back surface — Not fading. Color Venation Fully Opened, forward surface — No venation visible on labellum. Color Venation Fully Opened, back surface — No venation visible on labellum. Margin — Entire.

*Spurs*.—Quantity — Average of 1. Appearance — Short triangular, in line with central lobe of labellum. Length — Approximately 0.9 cm. Width — Approximately 0.4 cm. Height — Approximately 0.8 cm (at the base). Shape — Short triangular. Apex — Obtuse. Base — Broad cuneate. Margin — Entire. Texture — Glabrous, very slightly glossy. Color — Yellow-green; near RHS 145D.

*Sepals*.—Quantity — Average of 3. Appearance — One dorsal sepal (pointing upright) and two lateral sepals. Length — Dorsal sepal approximately 4.5 cm and lateral sepals approximately 4.2 cm. Width — Dorsal sepal approximately 5.9 cm and lateral sepals approximately 6.0 cm. Shape — Dorsal sepal broad ovate to near broad oblong. Lateral sepals broad ovate. Apex — Obtuse. Base — Cuneate. Margin — Entire, slightly coarsely undulate. Texture — Glabrous, matte, velvety. Color — Dorsal sepal green-white; near RHS 157D, violet-blue towards the margins; near RHS 92A to 92B. Sepal heavily dotted purple; near RHS 79A and N187A. Lateral sepals yellow-green; near RHS 145C and 150D, margins greyed-purple; near RHS N187B, Sepal heavily dotted purple; near RHS 79A and N187A.

*Pedicels*.—Length — Approximately 7.0 cm. Diameter — Approximately 0.6 cm. Angle — Approximately 80° angle to peduncle. Strength — Very strong. Texture — Glabrous, axially angled with 6 "ribs", axially twisted (due to resupination), glossy. Color — White; near RHS NN155C, proximal end coloured yellow-green; near RHS 145B.

Reproductive organs: Stamens, style and stigma fused into column? Yes.

*Column length*.—Approximately 0.6 cm.

*Column diameter*.—Approximately 0.8 cm.

*Column color*.—White; near RHS NN155B, under side green-white; near RHS 157B.

*Ovary position*.—Inferior.

*Ovary diameter*.—Approximately 0.4 cm.

*Ovary color*.—Green-white; near RHS 157D.

*Pollen color*.—Yellow-orange; near RHS 14A.

Seed and fruit: Seed production has not been observed.

Comparisons With Parent Plants

Plants of the new cultivar 'SPCDW1320' are similar to the seed parent, *Vanda* 'M58N' in most horticultural characteristics. However, the new variety exhibits cream yellow flowers overlaid with dense purple spotting and broad purple margins, whereas the seed parent exhibits cream flowers which are tinged blue and overlaid with dark blue spots.

Plants of the new cultivar 'SPCDW1320' are similar to the pollen parent, *Vanda* 'S399' in most horticultural characteristics. Plants of the new variety, however, are smaller, with a longer leaf span than the pollen parent.

Comparisons With Other Commercial *Vanda*

'SPCDW1320' is similar in most horticultural characteristics to the commercial variety *Vanda* 'Blue Magic' (not patented). The new variety, however, produces sepals and petals of which the coloration is a light yellow background with purple spotting and a broad rim of purple of each of the sepals and petals, the light yellow background being more prominent in the two lateral sepals then in the two petals and the dorsal sepal, whereas 'Blue Magic' produces petals and sepals that are white with thick, dark purple netting. The new variety has flowers which are similar in size as 'Blue Magic'.

That which is claimed is:

1. A new and distinct variety of *Vanda* plant named 'SPCDW1320', substantially as described and illustrated herein.

* * * * *